(12) United States Patent
Stetten

(10) Patent No.: US 8,981,914 B1
(45) Date of Patent: Mar. 17, 2015

(54) PORTABLE HAPTIC FORCE MAGNIFIER

(75) Inventor: George DeWitt Stetten, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 162 days.

(21) Appl. No.: 13/246,216

(22) Filed: Sep. 27, 2011

Related U.S. Application Data

(60) Provisional application No. 61/386,659, filed on Sep. 27, 2010, provisional application No. 61/494,955, filed on Jun. 9, 2011.

(51) Int. Cl.
*H04B 3/36* (2006.01)

(52) U.S. Cl.
USPC ............................................. 340/407.1; 606/1

(58) Field of Classification Search
CPC ................. A61B 2019/464; A61B 2019/2292; A61B 19/22; A61B 19/2203; A61B 19/5212
USPC ......... 340/407.1–407.2; 600/417, 429; 606/1, 606/130
See application file for complete search history.

(56) References Cited

U.S. PATENT DOCUMENTS

| | | | |
|---|---|---|---|
| 5,368,597 A * | 11/1994 | Pagedas .......................... 606/114 |
| 6,385,509 B2 | 5/2002 | Das et al. |
| 6,587,750 B2 | 7/2003 | Gerbi et al. |
| 6,969,384 B2 | 11/2005 | de Juan, Jr. et al. |
| 7,236,618 B1 | 6/2007 | Chui et al. |
| 7,373,219 B2 | 5/2008 | Nowlin et al. |
| 7,402,159 B2 | 7/2008 | Loesel et al. |
| 7,780,651 B2 | 8/2010 | Madhani et al. |
| 2004/0111029 A1 | 6/2004 | Bates et al. |
| 2004/0116906 A1* | 6/2004 | Lipow ................................ 606/1 |
| 2004/0215385 A1* | 10/2004 | Aizawa et al. ................... 701/93 |
| 2005/0119680 A1* | 6/2005 | Dykes ............................ 606/167 |
| 2006/0161045 A1* | 7/2006 | Merril et al. ................... 600/117 |
| 2006/0209019 A1* | 9/2006 | Hu ................................. 345/156 |
| 2007/0250078 A1* | 10/2007 | Stuart ............................ 606/130 |
| 2008/0153590 A1 | 6/2008 | Ombrellaro et al. |
| 2008/0161677 A1* | 7/2008 | Sutherland et al. ........... 600/417 |

(Continued)

FOREIGN PATENT DOCUMENTS

| | | | |
|---|---|---|---|
| EP | 1862134 A2 * | 12/2007 | ............. A61B 17/32 |
| JP | 2011200666 | 10/2011 | |

(Continued)

OTHER PUBLICATIONS

Search Report and Written Opinion for corresponding International Application No. PCT/US2011/053394 dated Feb. 21, 2012.

*Primary Examiner* — Hai Phan
*Assistant Examiner* — Orlando Bousono
(74) *Attorney, Agent, or Firm* — Klarquist Sparkman, LLP

(57) ABSTRACT

An improved system for magnifying forces perceived by an operator performing delicate procedures with a tool. The system senses forces between the tip and handle of the tool and actuates forces between the handle held by the operator and a brace contacting some other portion of the operator's anatomy. Magnifying the forces felt at the tip provides the ability to perceive forces that are smaller than could otherwise be felt and to perform procedures that are more delicate than possible without such enhanced perception. In at least one embodiment, the device is completely hand-held and thus can easily be adapted to a wide variety of locations, orientations, and applications.

18 Claims, 3 Drawing Sheets

(56) References Cited

U.S. PATENT DOCUMENTS

| | | |
|---|---|---|
| 2008/0226134 A1 | 9/2008 | Stetten et al. |
| 2008/0243177 A1 | 10/2008 | Oren et al. |
| 2009/0163929 A1 * | 6/2009 | Yeung et al. .................. 606/130 |
| 2009/0263775 A1 * | 10/2009 | Ullrich .......................... 434/267 |
| 2010/0134327 A1 | 6/2010 | Dinh et al. |
| 2010/0161129 A1 | 6/2010 | Costa et al. |
| 2010/0168918 A1 | 7/2010 | Zhao et al. |
| 2010/0179587 A1 * | 7/2010 | Grant et al. ................... 606/205 |
| 2010/0298843 A1 | 11/2010 | Blumenkranz et al. |
| 2010/0332030 A1 | 12/2010 | Larkin et al. |
| 2011/0046659 A1 * | 2/2011 | Ramstein et al. ............. 606/205 |
| 2011/0212427 A1 | 9/2011 | Kukora et al. |
| 2011/0277576 A1 | 11/2011 | Cooper |
| 2011/0277580 A1 | 11/2011 | Cooper et al. |
| 2012/0078164 A1 | 3/2012 | Mulvihill et al. |

FOREIGN PATENT DOCUMENTS

| | | | |
|---|---|---|---|
| WO | WO 95/20787 A1 * | 8/1995 | ................ G06F 3/00 |
| WO | WO 2008/054856 A2 * | 5/2008 | ............. G06F 3/041 |
| WO | WO 2008/074081 A1 * | 6/2008 | ............. B25J 13/02 |
| WO | 2011002592 | 1/2011 | |
| WO | 2011019878 | 2/2011 | |

* cited by examiner

PORTABLE HAPTIC FORCE MAGNIFIER

RELATED APPLICATIONS

This application claims the benefit under 35 U.S.C. §119 (e) of the earlier filing date of U.S. Provisional Application Ser. No. 61/386,659 filed on Sep. 27, 2010 and Ser. No. 61/494,955 filed on Jun. 9, 2011.

BACKGROUND OF THE INVENTION

1. Field of the Invention

The present invention relates to apparatuses that enhance the sense of touch for an operator using the apparatuses. The apparatuses have general utility in numerous fields where delicate procedures are undertaken, including surgery.

2. Background of the Invention

A need exists for improvement in the perception of forces by the sense of touch when performing delicate procedures. This is especially crucial when using tools in microsurgery. For example, surgeons routinely repair tiny blood vessels under a microscope that are far too delicate to be felt by the hand of the surgeon. Another key area for potential applications is ophthalmology, in which surgeons routinely pull delicate membranes off the retina that are far too flimsy to be felt by the surgeon. Providing a useful sense of touch for such applications would improve their outcome and increase the safety of the procedures.

Purely telerobotic systems such as the DA VINCI® Surgical System (Intuitive Surgical, Inc., Sunnyvale, Calif.) can provide motion-scaling, so that fine motion of the tool can be controlled by coarser motion of the operator's hand on the controls. Although force at the tool tip cannot be sensed by the operator in the current commercial DA VINCI® device, experimental systems have been tested that translate these forces into visual cues (Bethea, B., Okamura, A., Kitagawa, M., Fitton, T., Cattaneo, S., Gott, V., Baumgartner, W., Yuy, D. Application of Haptic Feedback to Robotic Surgery, J Laparoendosc, *Adv. Surg. Tech. A,* 14(3): 191-195, 2004) as well as into vibrotactile feedback to the operators fingers (Katherine J. Kuchenbecker, Gewirtz, J., McMahan, W., Standish, D., Martin, P., Bohren, J., Pierre P., Mendoza, J., Lee, D. VerroTouch: High-Frequency Acceleration Feedback for Telerobotic Surgery, *LNCS,* Volume 6191/2010, 189-196, 2010).

A different, non-telerobotic approach has been demonstrated in several experimental systems, including the Force-Reflecting Motion-Scaling System disclosed by Salcudean, et al. (Salcudean S. E., Yan J.: Motion scaling teleoperating system with force feedback suitable for microsurgery, U.S. Pat. No. 5,382,885 (1995); and Salcudean S. E., Yan J. (Towards a Force-Reflecting Motion-Scaling System for Microsurgery, *IEEE International Conference on Robotics and Automation,* San Diego, Calif., 1994), and the Steady Hand Robot described by Taylor, et al. (Taylor, R., Barnes, A., Kumar, R., Gupta, P., Wang, Z., Jensen, P., Whitcomb, L., deJuan, E., Stoianovici, D., Kavoussi, L.: A Steady-Hand Robotic System for Microsurgical Augmentation, *MICCAI,* Lecture Notes in Computer Science, Volume 1679/1999, 1031-1041, 1999, and Fleming, I., Balicki, M., Koo, J., Iordachita, I., Mitchell, B., Handa, J., Hager, G., and Taylor, R., Cooperative Robot Assistant for Retinal Microsurgery, *MICCAI* 2008, Part II, LNCS 5242, pp. 543-550, 2008). These systems generate a magnified sense of touch by using a robotic arm that holds the surgical tool simultaneously with the surgeon, pushing and pulling as appropriate, to amplify the forces detected by small sensors between the handle of the tool and its tip. Because every force needs an opposing force, the robotic arm must be mounted, and because of its large size, the mounting that supports the device is substantial. Thus, the magnified forces in these systems are created between the tool handle and subsequently the floor, via the robotic arm.

To permit free motion of the tool by the surgeon, an elaborate remote-center-of-motion articulated robot arm is employed, along with a control system to keep the tool moving naturally, as if controlled just by the operator, so that the surgeon can have something approaching the degrees of freedom and ease of manipulation that he/she is accustomed to with a freely held tool. Such systems are typically fairly extensive and complex. Issues involving the limited and congested workspace common in microsurgery raise serious challenges to practical deployment.

The goal of freeing robotic surgery devices from the floor-standing/mounted robotic arm has led to hand-held systems such as the MICRON microsurgical instrument from Riviere's group, which uses piezoelectric actuators to move the tip relative to the handle, based on optical tracking of both the tip and handle. Tabars, J., MacLachlan, R., Ettensohn, C., Riviere, C.: Cell Micromanipulation with an Active Handheld Micromanipulator, 32nd *Annual International Conference of the IEEE EMBS,* Buenos Aires, Argentina, 2010. The primary goal of MICRON is to reduce the effects of hand tremor. It is not suited to provide a magnified sense of touch because it has no actuator between the handle of the tool and something other than the target.

Yau, et al., have developed the hand-held "MicroTactus" tool for amplifying the sense of surface textures measured at the tool tip. Yau et al. achieve this result by using an inertial actuator in the tool's handle, which can only produce changing forces whose average is zero. The device disclosed therein does not include a brace against which non-zero-average forces can be exerted by the actuator, thus limiting its utility (H. Yau, V. Hayward, R. Ellis, "A Tactile Magnification Instrument for Minimally Invasive Surgery," *MICCAI* 2004, LNCS 3217, pp. 89-96.).

When the goal is to create non-zero average forces for the operator to feel, some external frame to "push against" has generally been employed. The field of haptic simulation faces the same dilemma of generating forces for the fingers to feel without anchoring the renderer to some solid base. Recent examples of more portable solutions include the "active thimble" described by Solazzi (Solazzi, et al. "Design of a Novel Finger Haptic Interface for Contact and Orientation Display," *IEEE Haptics Symposium* 2010, 25-26 March, Waltham, Mass., USA). The device is entirely mounted on one hand. It attaches to the proximal part of the finger and reaches over the finger to contact the fingertip, thus generating forces between two parts of the operator's own anatomy. As described in the above-referenced publication, "[a] limit of traditional kinesthetic interfaces is the difficulty to achieve a large workspace without a detriment of dynamic performance and transparency or without increasing the mechanical complexity. A possible solution to overcome this problem is to develop portable ungrounded devices that can display forces to the user hands or fingers."

The present invention addresses these long-standing needs by providing a haptic force magnifier that enhances the sense of touch of direct contact between a hand-held or finger-mounted device and a target that is being sensed or manipulated. The present invention achieves the enhanced sense of touch without requiring a robotic arm or any freestanding apparatus, but rather by producing forces between portions of the operator's own anatomy.

SUMMARY OF THE INVENTION

The present invention provides systems, methods, and apparatuses that provide an enhanced sense of touch. The present invention achieves this without needing to employ any virtual environment or any proxy robotic arms for manipulating the target. Instead, the present invention allows the operator to directly manipulate the object using common interfaces. In certain preferred embodiments, the present invention may be completely hand-held and light weight, or even mounted on a single finger, and is therefore easier to manipulate at a variety of angles or locations. The present invention replaces the robotic arm employed in prior art apparatuses by utilizing the operator's body itself to provide a moving platform from which the magnified forces are generated. The present invention preferably achieves an enhanced sense of touch in the operator by employing an actuator that amplifies forces that are generated at the tip of a sensing or manipulating tip. The present invention may be used in a wide variety of contexts, including medical, industrial, and experimental applications.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF PREFERRED EMBODIMENTS OF THE INVENTION

It is to be understood that the figures and descriptions of the present invention have been simplified to illustrate elements that are relevant for a clear understanding of the invention, while eliminated, for purposes of clarity, other elements that may be well known. The detailed description will be provided hereinbelow with reference to the attached drawings.

The present invention provides systems and methods for the enhancement of the sensation of touch. The device may be completely hand-held, or even mounted on a single finger, and therefore easier to manipulate to a variety of angles or locations when compared with the larger, bulkier systems of the prior art. These advantages allow the present invention to be implemented and utilized more easily and reliably because of its lighter weight, more localized forces, and simpler control system. The present invention preferably employs an actuator that magnifies forces that are generated at a sensing or manipulating surface that may be remote from the operator's body. The actuator magnifies the force preferably by using the operator's own body as the anchoring for the actuator, thus allowing free movement of the sensing device. Because of this attribute, the apparatuses of the present invention may be ungrounded and freely manipulated by the operator. The present invention may include a wide variety of sensing and manipulative attachments that directly interact with the target. The present invention achieves haptic enhancement without needing to use any robotic arm, thus allowing the operator to utilize a more natural device. While the present invention is particularly well suited for applications in surgery or other medical applications, it is equally well adapted for use in other situations (e.g., industrial or experimental) where it would be helpful to have the sense or touch enhanced due to the manipulation or sensing of small or delicate objects.

While the present invention is described herein using reference to particular configurations and tool tips, one of skill in the art will immediately recognize that these are simply exemplary. The present invention may include a wide variety of sensing and manipulating tips and may be adapted to accommodate any interface that the operator typically uses in the normal course of performing the task at hand.

Figure 1:
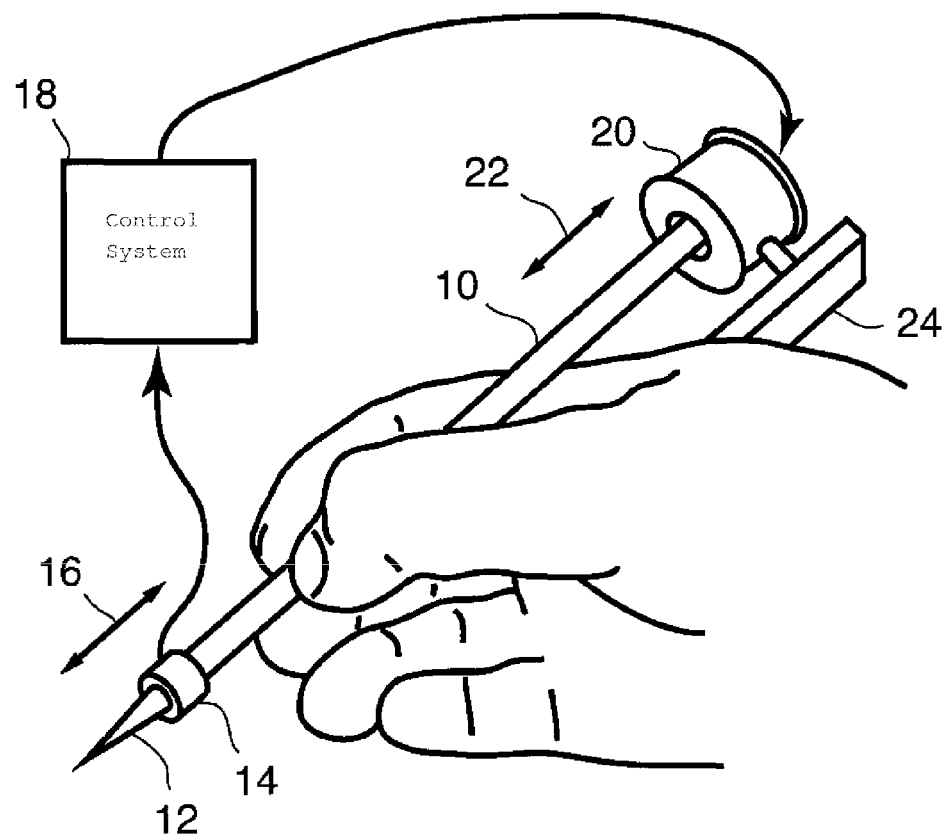
FIG. 1 shows an embodiment of the present invention based on forces generated between the fingertips and a brace over the hand.

One preferred embodiment of the present invention is illustrated in FIG. 1. A tool such as a surgical needle is held by the operator in the right hand with the thumb, index finger, and middle finger gripping the tool handle 10 as one would grip a pencil. The tool tip 12 as shown may be a sharp or blunt needle or other effector. A micro-force sensor 14 converts small detected forces (push or pull) 16 between the tip and the tool handle 10 into electrical signals that are transmitted to a control system 18. The control system causes the actuator 20, which may be a solenoid for example, to create a generated force 22 between the tool handle 10 and a brace 24 attached to the back of the hand. The control system 18 may simply be an amplifier to produce a force from the actuator 20 proportional to, greater than, and in the same direction as, the forces 16 at the tool tip 12. When the operator presses the tip 12 against some object in the environment, this produces the haptic illusion that the operator is pressing the handle 10 towards the tip 12 with a greater force than is actually being applied at the tip 12, magnifying the sensation of touch while preserving more delicate forces on the object in the environment. Note that since both pushing and pulling forces at the tip can be magnified, tool tips such as hooks are possible as well as needles.

Other embodiments are also contemplated as being within the scope of the present invention. For example, the apparatus could include a system to measure the position and orientation of the tip, handle, and brace relative to each other. This could be embodied, for example, as a displacement sensor based on an optical encoder, a potentiometer, or measurement of the electrical inductance of a solenoid, or by an external optical tracing tracking or imaging system. Knowledge of the tip location relative to the brace could be used by the control system to generate more accurate forces. An accelerometer could be used to determine the acceleration of the tool and its orientation with respect to the Earth's gravity. Various additional force sensors could be included to determine other forces between the fingertips and the tool handle, such as those employed with tweezers and scissors, with additional actuators to apply corresponding forces as appropriate. These embodiments merely provide examples of the wide variety of sensing and manipulating tools that can be implemented within the context of the present invention.

Forces detected at the tip of the tool and forces generated by the actuator could be in other directions than those shown in FIG. 1. Forces and torques in all directions could thus be sensed and enhanced. A wide variety of force sensors (silicon strain gauges, piezoelectric, piezoresistive, Bragg sensors, optical imaging of strain, etc.) and actuators (electromechanical, hydraulic, pneumatic, piezoelectric, etc.) are clearly available for embodiments of this invention. The actuators may include a number of pre-load components based on magnets, springs, and other sources of stable force. This would permit the detection of both push and pull from a single-mode sensor and could be otherwise useful in the design of the device.

Likewise, a wide variety of well-known control systems 18 may be used within the context of the present invention. The control system may be an analog circuit, a computer or embedded processor equipped with inputs and outputs, or other platform. The control system may employ a diversity of electronic components to generate signals to create the forces used in the context of the present invention. For example, the controller may utilize linear operational amplifiers or more elaborate computer systems to convert the signal arising from the force sensor into a force to be exerted on the operator through the tool via the actuator. The relationship between those two forces may be linear, logarithmic, or other non-linear function. For example, the control system may apply a simple linear gain to the signal from the force sensor to produce a control voltage for the actuator. To the extent that the force sensor is non-linear, table-lookup or parametric linearization of the sensor signal may be employed.

With sufficient gain, instability may lead to oscillation, and standard methods such as a Proportional-Integral-Differential (PID) control may be used to reduce or eliminate such oscillations. Data from other sensors such as force, location, or orientation, or other parameters such as temperature, magnetic field, resistance, capacitance, inductance, or reluctance from various parts of the device could be used to improve its operation. These data may be used to assess proper functioning of the force sensor and actuator, as well as provide additional information (e.g., information regarding the Earth's magnetic field through magnetic sensors, actuator coil temperature to confirm actuator performance, and ultrasound data to provide visual guidance to the operator). Data could be recorded for later analysis or for incorporation into adaptive control processes.

Finally, as with many systems that measure force, calibration includes setting the zero point when no external force (besides gravity) is being applied to the sensor. This is often accomplished by activating a manual control (sometimes labeled "tare" or "unladen weight" on weighing platforms), which establishes the present reading from the force sensor as "zero." In the present invention, such a zero point may depend upon the orientation of the device with respect to gravity, the effects of temperature, or the particular state of hysteresis in the various mechanical components of the force sensor. Automating this process is problematic, since it is not always obvious when the desired calibration is to be performed. Since the sensing or manipulative tip is on the end of a hand-held tool, the present invention can take advantage of the fact that when the tip is touching something there will unavoidably be some temporal variation in the signal from the force sensor due to hand tremor. Thus, the control system could automatically calibrate the zero point of the force reading whenever the force sensor detects an appropriately long period of inactivity. This would also permit canceling of gravitational forces in different tool orientations with respect to the earth, by simply holding the tool steady after changing it to a new orientation. This automated calibration method may increase the useful sensitivity of the system, especially with inexpensive force sensors, by reducing problems due to inherent drift and hysteresis.

Although FIG. 1 shows a needle tip, a wide variety of other tools are possible, such as forceps, scissors, hooks, scrapers, and cutting blades. For tools such as forceps and scissors, forces between the moving parts could also be magnified for the operator using the same principles disclosed herein.

Figure 2:
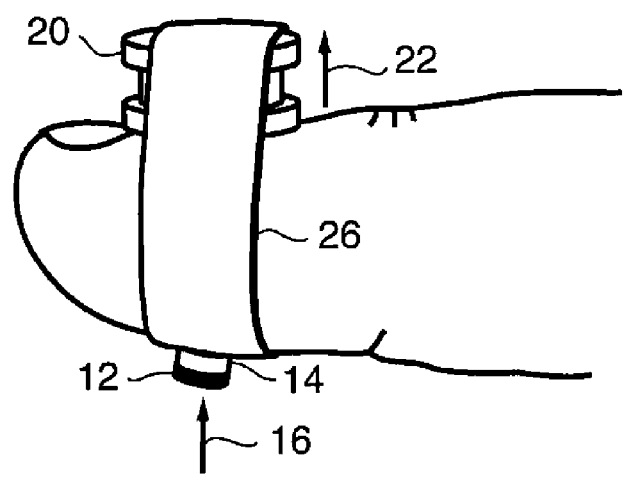
FIG. 2 displays an embodiment of the present invention based on forces generated between the tip of a finger and the back of the same finger.
Figure 3:
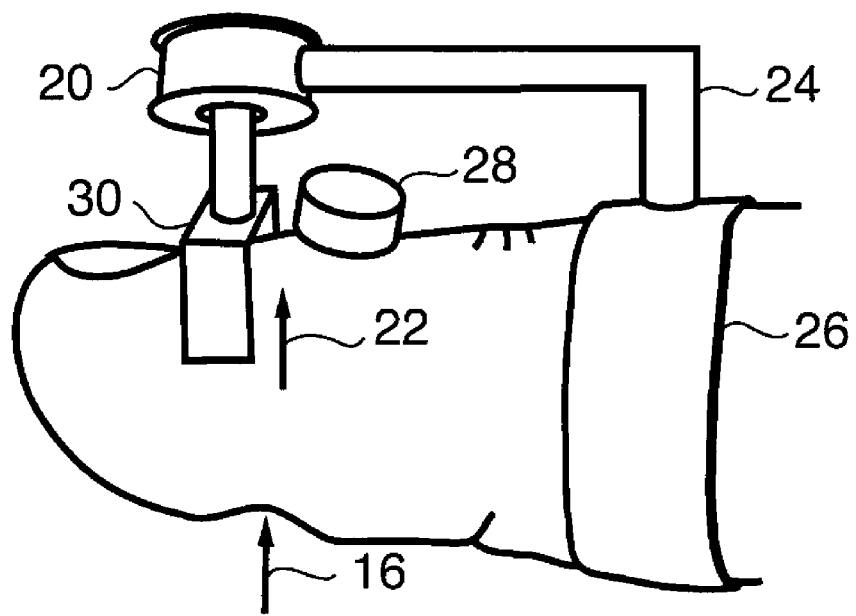
FIG. 3 provides an embodiment of the present invention whereby the direct sense of touch of a finger may be amplified.

Although FIGS. 1, 2, and 3 show the actuator generating forces between parts of the same hand, other parts of the operator's anatomy, including the wrist, upper arm, or other hand, could be used to contact the brace.

While FIG. 1 shows the force sensor 14 and actuator 20 connected to a control system 18 detached from the operator's hand, the entire apparatus including the control system could be worn by the operator in some embodiments, or the communication between the various parts including some of which could be remote from the operator could be wireless.

A mechanism can be envisioned for providing a failsafe mechanism within the context of the present invention for preventing unduly strong forces from being exerted by the tool tip. For example, weak points between the actuator and the tool tip could break, crumple, or disconnect to prevent excess force generated by the actuator from reaching the tip where it might damage the object being contacted. Various other well-known failsafe mechanisms could be incorporated into the control system itself.

Sterilization is crucial for most surgical procedures. The present invention could be built into a sterile surgical glove, providing a number of key advantages. In some embodiments, it would permit direct contact between the surgeon's fingers and the tool, rather than though a separate glove, for better sensation. The forces from the tool could be spread over the hand by the glove, without requiring a separate brace to be put on after putting on a surgical glove. Thus the glove could act as the brace itself. Various arrangements could be employed so that the tool would not need to be attached continually during the operation by the surgeon, for example, by having specialized attachment points built into the surgical glove for various parts of the tool. Parts of the tool could thus be detachable from each other and from the glove, such that the specialized glove and less expensive parts of the tool could be disposable, while the more expensive parts of the tool (for example, the actuator) could be reused after sterilization.

The present invention also contemplates the use of non-rigid tools. In particular, it can apply to tools with a flexible section between the tip and handle, such as catheters, so long as axial force and/or torque can still be transmitted to the tip by the operator. Such embodiments could prove particularly useful in catheters with steerable tips, for feeling one's way into the branches of an artery, for example. Many catheters are operated from a handle that is essentially hand-held, and this could easily be adapted use within the context of the present invention for force magnification by the addition of a brace and an actuator.

A different embodiment of the invention is shown in FIG. 2. Here the portion of the device that touches the operator is not the handle of a tool but rather a strap 26 around the finger. The point of contact with the object in the environment is still labeled tool tip 12, which is mounted with a micro-force sensor 14 directly behind it, on the opposite side of the strap 26 from the pad of the finger. The strap 26 may wrap around the back of the finger to act also as the brace against which an actuator 20 creates a force 22, which is in the same direction but with a greater magnitude than the force 16 measured by the force sensor 14, as controlled by a control system (not shown). This embodiment of the present invention would allow an operator to experience a dramatically enhanced sense of touch, for example, when evaluating a surface.

In yet another embodiment, the tip that touches the object in the environment is the fingertip itself. The fingertip is also employed as the force sensor by measuring the compression of the fingertip by a force 16 from contact with an object in the environment using an ultrasound transducer 28 (or other method of measuring compression such as redness in the fingernail bed) mounted on the top of the finger. The ultrasound transducer would allow imaging of deformation in the internal structure of the finger, which would correspond to the forces being felt by the fingertip. Any other device that would allow measurement of the forces encountered by the surface of the finger could be used, including monitoring the electrical responses in the nerves of the fingertip. The actuator 20 is attached between the top of the distal phalanx of that finger and a brace 24 extending from the middle phalanx of the same finger to which it is attached with a strap 26, such that the actuator can pull back the distal phalanx with force 22 using a clip 30 attached to the top of the distal phalanx. Amplification of the measured distortion by the control system (not shown) controlling the actuator causes magnification of the muscle force required to press with a certain force on the object, and thus an increased sense of the force between the object in the environment and the fingertip.

The actual sensation of force from the sensory endings in the fingertip may, however, be reduced by this arrangement. To address this, the embodiment may be adapted by reversing the direction of force 22 (opposite from the direction shown in FIG. 3) so that it pushes the finger further against the object in the environment, intensifying the sensation of contact with that object. By knowing both the magnitude of force 16 from the compression of the fingertip and force 22 that the actuator is exerting, the control system could compute the difference between the forces, which would be that force against the object in the environment being exerted by the finger muscles themselves, and adjust force 22 so that the combined force is some desired multiple of that force. Thus this adaptation would create a magnified sense of touch in the nerve endings of the fingertip for the force delivered by the muscles themselves. Therefore it may be seen that nothing in the phrase "force magnifier" should exclude any particular implementation of relation between the measured force and the actuator force.

Nothing in the above and attached descriptions is meant to limit the present invention to any specific materials, geometry, or orientation of elements.

Many modifications are contemplated within the scope of the present invention and will be apparent to those skilled in the art. The embodiments disclosed herein were presented by way of example only and should not be used to limit the scope of the invention.

What is claimed is:

1. A device for magnifying physical sensations using haptic forces to a hand of an operator, the hand including a main body and fingers extending from the main body, the device comprising:
   a tool, including a handle adapted to be held by the operator and a tip for interacting with an object;
   a control system;
   a force sensor that assesses force between the tip and the object to determine a detected force on the tool by the object and converts the detected force into electrical signals that are transmitted to the control system;
   a brace that contacts one or more points on the main body of the hand of the operator and contacts the tool, the brace being configured to be attached to the main body of the hand; and
   a force actuator between the tool and the brace, the force actuator coupled to the brace via a connecting member;
   wherein the control system receives information from the force sensor about the force between the tip and the object and generates a magnifying force to be exerted against the brace through the force actuator in the direction of the detected force with a magnitude that corresponds to the amount of the detected force so that a physical sensation of the operator is magnified, and
   wherein the connecting member transfers the generated magnifying force to the brace.

2. The device of claim 1, wherein the magnifying force to be exerted against the brace is a force greater than the detected force.

3. The device of claim 1, further comprising a measuring system to measure the position, orientation, or motion of the tool, operator's anatomy, and brace relative to each other.

4. The device of claim 1, further comprising a failsafe mechanism to prevent damaging force from being exerted on the object in the environment.

5. The device of claim 1, wherein one or more parts of the device are integrated into a glove.

6. The device of claim 1, wherein one or more parts of the device are detachable.

7. The device of claim 1, wherein one or more parts of the device are adapted to be sterilized.

8. The device of claim 1, wherein the control system automatically calibrates the force actuator to produce zero force when a period of inactivity is detected in the force sensor.

9. The device of claim 1, further comprising a sensor for gravity.

10. The device of claim 1, wherein the handle is adapted to be held between at least two of the operator's fingers.

11. The device of claim 1, wherein the handle is rigid.

12. The device of claim 1, wherein the handle is flexible.

13. The device of claim 1, wherein the tip is a needle, a hook, a scraper, a forceps, a scissors, or a cutting blade.

14. A device for magnifying physical sensations of an operator using haptic forces to a hand of an operator, the hand including a main body and fingers extending from the main body, the device comprising:
   a tool having a longitudinally-extending body that defines a longitudinal axis, including a handle adapted to be held by the operator and a tip for interacting with an object;
   a control system;
   a force sensor that assesses force between the tip and the object to determine a detected force on the tool by the object along or about the longitudinal axis and converts the detected force into electrical signals that are transmitted to the control system;
   a brace that contacts one or more points on the main body of the hand of the operator and contacts the tool, the brace being configured to be attached to the main body of the hand; and
   a force actuator between the tool and the brace;
   wherein the control system receives information from the force sensor about the force between the tip and the object and generates a magnifying force along or about the longitudinal axis to be exerted against the brace through the force actuator in the direction of the detected force with a magnitude that corresponds to the amount of the detected force so that a physical sensation of the operator is magnified, and
   wherein the force actuator is coupled to the brace via a connecting member that transfers the generated magnifying force to the brace along an axis that is offset from the longitudinal axis.

15. The device of claim 14, wherein the magnifying force to be exerted against the brace is a force greater than the detected force.

16. The device of claim 14, further comprising a measuring system to measure the position, orientation, or motion of the tool, operator's anatomy, and brace relative to each other.

17. The device of claim 14, further comprising a failsafe mechanism to prevent damaging force from being exerted on the object in the environment.

18. The device of claim 14, wherein one or more parts of the device are integrated into a glove.

\* \* \* \* \*